United States Patent [19]

Kuntz

[11] 4,424,815

[45] Jan. 10, 1984

[54] STETHOSCOPE-TYPE RECORDING SYSTEM WITH STRETCHED-IN-TIME PLAYBACK

[76] Inventor: David H. Kuntz, 11810 Bel Ter., Los Angeles, Calif. 90049

[21] Appl. No.: 196,469

[22] Filed: Oct. 14, 1980

[51] Int. Cl.³ .............................................. A61B 5/00
[52] U.S. Cl. ................................ 128/715; 346/33 ME
[58] Field of Search ............ 128/715, 773; 179/1 ST; 346/33 ME

[56] References Cited

U.S. PATENT DOCUMENTS 3,867,715 2/1975 Geil .................................... 367/132

FOREIGN PATENT DOCUMENTS 637855 3/1962 Canada ................................ 128/715

OTHER PUBLICATIONS

Holloway, G. A. et al, "An Electronic Frequency Shifting Stethoscope For Heart Sounds", Trul Broeng V2 pp. 59-64 #12 Apr. 1978.

Primary Examiner—Kyle L. Howell
Assistant Examiner—Francis J. Jaworski
Attorney, Agent, or Firm—Henry M. Bissell

[57] ABSTRACT

A system for recording heart sounds from a stethoscope-type device and reproducing selected heartbeats stretched out in time but with the same pitch as recorded. In one embodiment the heart sounds are sampled and converted to a digital representations which are recorded on a tape recorder at a first speed. The tape recorder is of the endless loop recording and playback type. At a signal from the user, the tape recorder plays back at a reduced speed the last few heartbeats which are recorded. These are converted to analog signals and fed back to the transducer in the stethoscope for reproduction as natural heartbeat sounds merely stretched in time.

Another system records the heartbeat sounds on a rotating recorder such as a magnetic drum. The magnetic transducer may be driven at variable speeds so that, when activated by the user, the speed of the playback transducer is reduced relative to the speed of the transducer during recording, without reducing the rotational speed of the drum. Thus, the pitch of the heart sounds is not affected, although they are stretched out in time.

Another embodiment utilizes a delay line for temporary storage with scanning of selected taps in the delay line for storage of selected samples in the memory. Upon activation by the user, the stored samples in the memory are read out at a reduced rate, filtered for smoothing, and fed back to the stethoscope transducer for reproduction as stretched heartbeat signals at the original pitch.

18 Claims, 3 Drawing Figures

STETHOSCOPE-TYPE RECORDING SYSTEM WITH STRETCHED-IN-TIME PLAYBACK

BACKGROUND OF THE INVENTION

1. Field of the Invention

This invention relates to recording and reproducing systems for heart sounds and, more particularly, to such systems having the capability of recording heart sounds from a stethoscope and playing them back through the stethoscope at a reduced signal rate but at the natural pitch.

2. Description of the Prior Art

Physicians and others have been accustomed to listening to heart sounds for centuries. The invention of the stethoscope is attributed to R. T. H. Laennec who, in 1816, used a wooden cylinder to transmit heart sounds to the ear. Acoustic stethoscopes are used to investigate the condition of the respiratory, circulatory and digestive systems. Most sounds of interest to a doctor, especially heart sounds, have frequencies in the range from 60 to 600 Hz, but some mitral diastolic murmurs (irregular sounds heard over the heart during expansion of the heart and indicating an abnormality in the mitral valve) have frequencies below 60 Hz; a few sounds, such as crepitations (crackling sounds heard over the chest in some diseases of the lungs), have frequencies up to about 1400 Hz. Acoustic stethoscopes do not amplify sound; they merely convey it to the ear in as efficient a manner as possible.

Phonocardiographs are devices for monitoring heart sounds electronically. A phonocardiograph gathers no more information than a simple acoustic stethoscope, but it displays the sound in visual form on a cathode ray tube or pen recorder, sometimes making diagnosis simpler. Electrocardiograms are also used to diagnose heart valve defects. These, however, are recordings or displays of voltage patterns, rather than heart sounds, which are generated by the heart muscles. The medical field has long been aware of the use of digital computers in the analysis of electrocardiac signals and the automatic measurements of various parameters in the heart wave as developed in an electrocardiogram. Some early studies in this area, initiated by Dr. Cesar A. Caceres, then of the United States Public Health Service, have been reported, among others, in "Pattern Recognition in the Clinical Electrocardiogram" by Caceres et al, IRE TRANSACTIONS ON BIO-MEDICAL ELECTRONICS, January 1962.

Despite the capability of the prior art to analyze electrical signals from the heart, such developments do not deal with analysis of heart sounds. They may provide correlative information but they require equipment which is vastly more complex than the simple stethoscope with which every doctor is familiar and is generally equipped. There are examples in the prior art of attempts to make heart and other body sounds, particularly of low and almost inaudible frequencies, more readily audible by conversion into a higher frequency range. See for example Gregg U.S. Pat. No. 3,348,535, Massie U.S. Pat. No. 3,601,120 and the British U.S. Pat. No. 1,008,027. These, however, unavoidably alter the character of the sounds thus converted and, accordingly, do not deal with the objective of processing heart sounds to provide a result which is unaltered as to pitch, and therefore will be familiar to the practitioner, but stretched out in time so that the practitioner can more readily distinguish and analyze the individual portions of the cyclic heartbeat sound. Furthermore, these patented systems do not deal with the desirable feature of permitting the practitioner to repeat, stretched out in time, a heart cycle or a few cycles which he has just heard and would like to hear again.

Stethoscope recording systems are well known in the prior art. For examples of such, see U.S. Pat. Nos. 3,052,756 of Seven et al, 3,188,645 of Trumpy et al, and 3,846,585 of Slosberg et al. However, these only provide the capability of repeatedly reproducing the recorded heart sounds for further study, with the advantage of amplification and tonal modification, if desired.

So-called "electronic stethoscopes" have been disclosed, for example, in U.S. Pat. Nos. 3,160,708 of Andries et al, 3,132,208 of Dymski et al, 3,247,324 of Cefaly et al, and 4,170,717 of Walshe. Typically, however, these disclosures merely deal with the capability of amplifying the sounds picked up by the stethoscope and possibly processing the heartbeat signals to remove undesired sounds so that other sounds can be amplified, studied and/or recorded without interference from the undesired sounds.

Systems are known for the time compression and expansion of audio signals. Those of which I am aware generally depend upon very sophisticated and complex equipment, as well as techniques and concepts, and are designed for dealing with audio signals other than heart and body sounds. One such system of Kitamura, disclosed in U.S. Pat. No. 3,975,763, operates with signals having been reproduced with a frequency spectrum scale differing from that at the time of recording. The Kitamura et al U.S. Pat. No. 4,020,291 utilizes a filter for filtering the fundamental frequency component of an input signal reproduced at a speed differing from that at the time of recording to produce a time compressed or expanded signal synchronized with the pitch period of the fundamental frequency component of the input signal. Boothroyd in U.S. Pat. No. 3,520,996 discloses apparatus for playing back an original recording at a slower speed with reduced pitch. The signal is then processed by delay line sampling in a reverse direction to increase the pitch, and thereafter the samples are inserted periodically into the original record to extend the playback time. Schiffman in U.S. Pat. No. 3,828,361 discloses storage of speech signals in analog shift registers with control of the shift rate in accordance with reproducer input speed so that normal frequency sounds are developed, regardless of input pitch level or transducer speed.

Despite these examples of prior art developments, the problem still remains of adequately dealing with the transitory nature of heart sounds which the physician hears through his stethoscope and processing them so that he is able to hear the sounds in the same manner and at normal pitch but stretched out in time. Heart sounds are audible representations of certain physical events, notably closure of certain valves and alterations in fluid flow. The sounds generated by these events vary in duration, pitch, timbre, volume and sequence. It is by interpretation of these sounds that the sophisticated ear can infer the presence of disease and often the nature of such disease. These various sounds occur in rapid succession and may actually overlap one another. Rapid heart rates shorten the duration of each heart cycle, rendering interpretation of these sounds more difficult. Simple amplification may assist in low volume problems or problems of high ambient noise, and selective frequency amplification may aid in interpretation. However the principal problem is the compression of all of the pertinent information into a short time span. The present invention is designed to stretch the duration of the cycle of heart sounds without altering the pitch, sequence, character and relative duration of these sounds, thus simplifying such interpretation by the ear of the examiner. In using the stethoscope, the practitioner would like to be able to select from time to time a few heartbeats, say five in sequence, and play them back for review. Desirably, these should be replayed stretched out in time, say five to ten times the real time interval, and without changing the pitch or other audible characteristics of the sounds.

SUMMARY OF THE INVENTION

In brief, arrangements in accordance with the present invention incorporate a stethoscope equipped with a transducer for converting heart/body sounds into electrical signals, apparatus for recording or storing signals corresponding to the signals from the stethoscope, and an arrangement for reproducing selected ones of the recorded signals, preferably through the stethoscope by conversion from electrical to audio form via the stethoscope transducer. The reproduced signals are stretched out in time but of the same pitch as originally recorded. A switch and associated control stage are provided for the use of the practitioner to enable him to select the particular recorded signals which he would like to have "replayed" as processed by the equipment.

One particular arrangement in accordance with the invention utilizes a rotating magnetic medium, such as a drum or disk, with associated recording and/or reproducing transducers positioned to be selectively driven along a surface of the recording medium. In accordance with known techniques, the signals from the stethoscope transducer are modulated and recorded on the magnetic medium by the recording transducer moving at a first translational speed along the drum or disk. Upon command of the practitioner, the transducer movement is slowed to a second translational speed which results in the recorded signals being played back at a slower speed or stretched out in time. However, the pitch of the sounds is maintained unchanged, since this is dependent upon the rotational speed of the drum which is maintained constant.

In another particular arrangement in accordance with the invention, heart sound signals from the stethoscope transducer are converted to digital form and recorded on an endless loop tape recorder. Upon activation by the practitioner, the tape drive is reduced in speed and the recorded signals present on the endless loop are converted back to analog form, filtered for smoothing, and converted back into heart sounds via a headset. Since the digital values are unaffected by the change in speed of the tape recorder, the pitch of the reproduced sounds is the same, although they are stretched out in time.

Still another arrangement in accordance with the present invention involves the amplification of signals from the stethoscope transducer to a delay line having output taps positioned at regular intervals along the line. These taps are regularly scanned under the control of a clock, and thus the heart sound waveform in the delay line is sampled at discrete intervals adequate to maintain the signal content. From the scanner, the samples are stored in a memory and, upon activation by the practitioner, the memory is read out under the control of a memory clock operating at a lower pulse rate than the clock associated with the scanner and delay line. This readout signal is filtered and applied to a loudspeaker or to the stethoscope transducer for conversion into audible heart sounds, stretched out in time but maintained at original pitch.

Each of these arrangements provides the capability of playing back the selected portion of the signals repetitively, so that the reproduced stretched-in-time portion can be listened to again and again under the control of the user so that it can be studied and analyzed for diagnosis or for other reasons.

BRIEF DESCRIPTION OF THE DRAWING

A better understanding of the present invention may be had from a consideration of the following detailed description, taken in conjunction with accompanying drawing in which.

DETAILED DESCRIPTION

Figure 1:
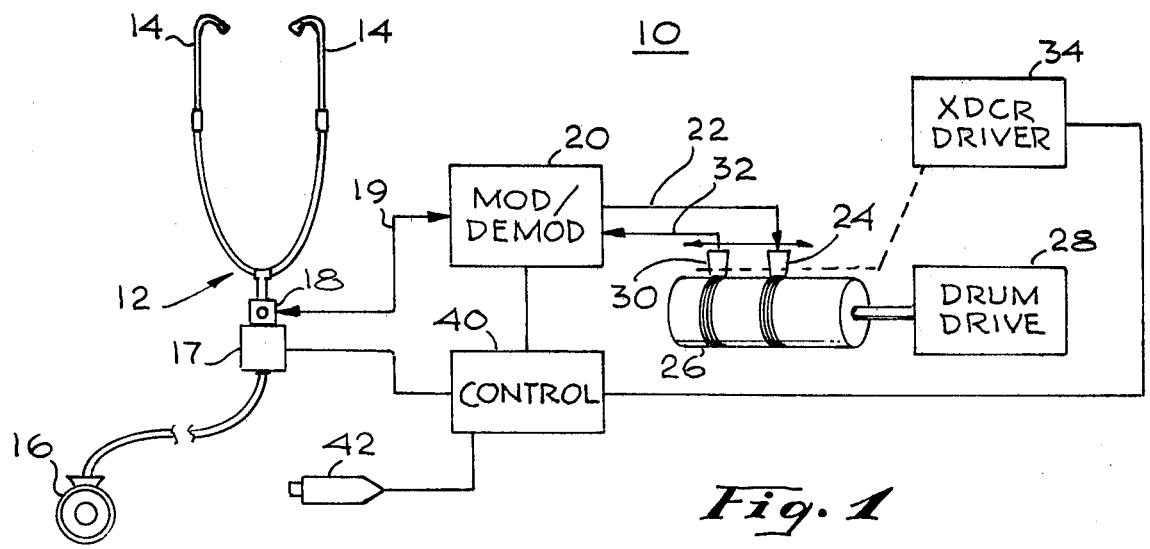
FIG. 1 is a block diagram of one particular arrangement in accordance with the present invention utilizing a magnetic drum as a recording and time conversion medium.

FIG. 1 illustrates in block diagram form a system 10 in accordance with one particular embodiment of the present invention. In the system 10 a modified stethoscope 12 having ear pieces 14 and a pickup 16 is equipped with a transducer 18 for converting acoustic vibrations into electrical signals and vice versa. A selectively operable "valve" 17, which may be a plastic tube and a constricting mechanism, is mounted in the tube between the pickup 16 and the location of the transducer 18. The electrical lead 19 from the transducer 18 is connected to a modulator/demodulator stage 20 having an output lead 22 connected to a recording transducer 24 associated with a magnetic drum 26 which is coupled to be driven at a constant rotational speed by a drum drive stage 28. A second, reproducing or playback transducer 30 is mounted adjacent the surface of the drum 26 to generate electrical signals corresponding to the magnetic states or imprints recorded on the drum surface. An electrical connection is provided between the playback transducer 30 and the modulator/demodulator stage 20 via a lead 32. A transducer drive stage 34 is shown mechanically coupled to the transducers 24, 30 to control their position and movement along the surface of the drum 26 parallel to the axis of rotation. If desired, the transducers 24, 30 may be combined in a single record/playback transducer and switched between recording and playback in accordance with known techniques. Also, if desired, the magnetic medium may comprise a disk instead of the drum 26. Alternatively, a magnetic belt may be substituted for the drum.

The system 10 of FIG. 1 further includes a control stage 40 coupled to respond to an associated switch 42 and control the modulator/demodulator stage 20 and the transducer drive stage 34 accordingly. In the operation of the system of FIG. 1, acoustic vibrations in the stethoscope 12, picked up from the body via the pickup 16, are converted into electrical signals by the transducer 18 and directed to the modulator portion of the stage 20. At this point, the stage 20 is in the condition to apply such signals to the recording transducer 24 for recording on the surface of the drum 26. During recording, the transducer drive stage 34 moves the transducers 24, 30 at a fixed rate of speed along the surface of the drum from left to right in FIG. 1. Thus, signals recorded by the transducer 24 may be reproduced by the transducer 30 a short time later by virtue of the fact that the transducer 30 follows the transducer 24 along the drum surface.

When the practitioner wishes to review a series of heartbeats which he has just heard via the stethoscope 12, he presses the switch 42 which causes the control stage 40 to switch the stage 20 into the demodulator mode and causes the transducer drive stage 34 to reduce the translational speed of the transducers 24, 30—particularly the playback transducer 30—to a fraction of its speed in the recording mode. For example, the speed for playback may be reduced to 1/5 the recording speed. As a result, the playback transducer 30 picks up the signals which were recorded on the surface of the drum 36 a predetermined time interval previously (depending upon the spacing between the transducers 24, 30 and the translational speed during recording) and proceeds to reproduce these signals at a rate which is 1/5 their rate of occurrence in real time. The reproduced signals are applied to the demodulator portion of the stage 20 via the lead 32 where they are demodulated and fed to the stethoscope transducer 18 for conversion into acoustic vibrations in the stethoscope 12. These acoustic vibrations represent the original heartbeat sounds stretched out in time by a factor of 5 times. However, the pitch of the sounds is unchanged, because it is dependent upon the rate of rotation of the drum 26, which is maintained without deviation. During this "review" mode, the control stage 40 also activates the valve 17 to block sounds from the pickup 16, thus preventing interference with the stretched-in-time sounds in the stethoscope 12. Release of the push button switch 42 restores the system to the modulating and recording mode and a subsequent series of heart sounds may be recorded for selective playback in similar fashion.

Particular details of a typical signal recording and reproducing portion of the system 10 of FIG. 1, involving the record medium, the electromagnetic transducers and the modulation/demodulation stage are set forth with particularity in the Zenzefilis U.S. Pat. No. 3,701,846, incorporated herein by reference as though set out in full. That patent discloses a method and apparatus for recording and reproducing television signals which include the sound portion of a transmitted television signal. As disclosed, the patented system modulates the intelligence for recording in a form of encoding known as PLC (Pulse Length Code) and the resultant signals are recorded as a series of imprints along the magnetic surface of a drum, disk or belt. In standard television signals, the sound is in the form of signals placed at unused portions of the picture signal, such as the trailing edge of synchronizing signals. Therefore, the sound is included and recorded along with the video and the associated synchronizing signals. For playback, the pulse length code is demodulated and converted into signals of standard video and audio form.

In the arrangement of FIG. 1, since no video is involved, the system could operate using only the sound portions of the system disclosed in the patent. Alternatively, the electrical signals from the transducer 18 may be recorded directly in accordance with standard simplified techniques for audio recording, in which case the stage 20 may comprise a simple switch for transferring the connection to the lead 19 between the leads 22 and 32 when the control stage 40 shifts between recording and playback modes.

Figure 2:
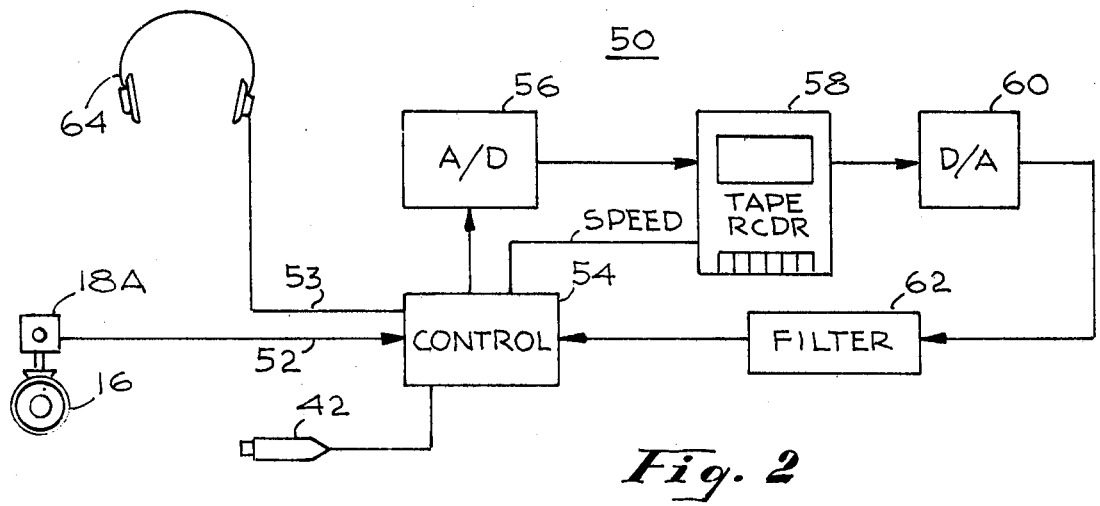
FIG. 2 is a block diagram of another particular arrangement in accordance with the present invention utilizing a tape recorder for storage of signals in digital form for readout at reduced speed and stretched out in time.

FIG. 2 illustrates a second system 50 in accordance with the invention utilizing an alternative sound transducing device. The sound pickup 16 is coupled to a transducer 18A which applies corresponding electrical signals via lead 52 to a control stage 54 which provides switching and control of the associated circuitry. As shown in FIG. 2, a signal path extends from the control stage 54 to an analog-to-digital (A/D) stage 56, the output of which is directed to a tape recorder 58. Since the output of the A/D stage 56 is in digital form, the tape recorder 58 has the capability of recording digital signals. The tape recorder 58 is of the endless loop type, in which a continuous tape loop is provided for recording a limited amount of signal information and playing back the information with a predetermined delay dependent upon the spacing of the playback head from the recording head. From the tape recorder 58, the reproduced, delayed signal is directed to a digital-to-analog (D/A) stage 60, the output of which is an analog signal corresponding to the analog signal applied at the input of the A/D stage 56. The output of the A/D stage 60 is applied to a filter 62 for smoothing and then applied to the control stage 54. From there the signal is applied via a lead 53 to a headset 64. The control stage 54 operates in response to the switch 42 to feed signals to the headset 64 from either the transducer 18A or the filter 62, depending on whether the system is being operated by the user for listening to heart sounds in real time or stretched-in-time when in the review mode.

During the recording mode, a connection is established within the control stage 54 to apply signals from the lead 52 to the lead 53 and to the A/D converter 56 for recording in the tape recorder 58. The output of the recorder 58 is disregarded. When the practitioner wishes to review a series of heartbeats which he has heard from the stethoscope 12, he presses the push button switch 42 which activates the control stage 54, switching the connection to the lead 53 from the lead 52 and transferring it to the output of the filter 62. At this time, the control stage 54 also reduces the speed of the tape recorder 58 so that the recorded signals which are applied to the D/A stage 60 and ultimately to the headset 64 are stretched out in time. The length of the endless loop in the tape recorder 58 may be varied and determines the number of heartbeat cycles which will be played out in this fashion. As long as the switch 42 remains closed, the recorded portion of heartbeat cycles is played out repetitively for study by the user. Since the digital form of the signals recorded in the tape recorder 58 is unaffected by the change in speed, the pitch of the stretched signals is unaffected and, as before, the acoustic vibrations generated from the signals now fed into the headset 64 will approximate the natural heart sounds, merely slowed down.

A/D and D/A converters are well known in the prior art. A number of typical circuits and details relating to such are described in "A User's Handbook of D/A and A/D Converters" by Eugene R. Hnatek (John Wiley & Sons), incorporated herein by reference. A particular A/D converter type which may be used in the stage 56 of the system 50 of FIG. 2 is the Charge-Balancing A/D Converter described in the textbook beginning at page 255. A circuit of this type samples an input analog waveform and provides an output in the form of a number of regularly spaced clock pulses which is representative of the amplitude of the analog signal. A corresponding D/A converter, such as may be employed in the stage 60 of FIG. 2, converts digital signals in the form of numbers of regularly spaced clock pulses to analog signals of corresponding amplitude. Since it is the number of clock pulses, rather than the spacing or duration of the digital signal, which is used to determine the resulting analog signal, it will be appreciated that variations in speed of the tape recorder 58 will not affect the pitch of the recorded and reproduced signals, only their spatial distribution in time. Thus, the operation of the system of FIG. 2 as described results in the playback of the selected number of heartbeat sounds stretched out in time but maintained at natural pitch.

Other modulation/demodulation techniques may be employed in the practice of the present invention. Engelson et al in MICROWAVE JOURNAL, April, 1980, pp. 35ff, "Digital Radio Measurements", incorporated herein by reference, describe the use of such techniques to develop a time-division-multiplexed composite signal which may be processed, demodulated and restored to analog form.

Figure 3:
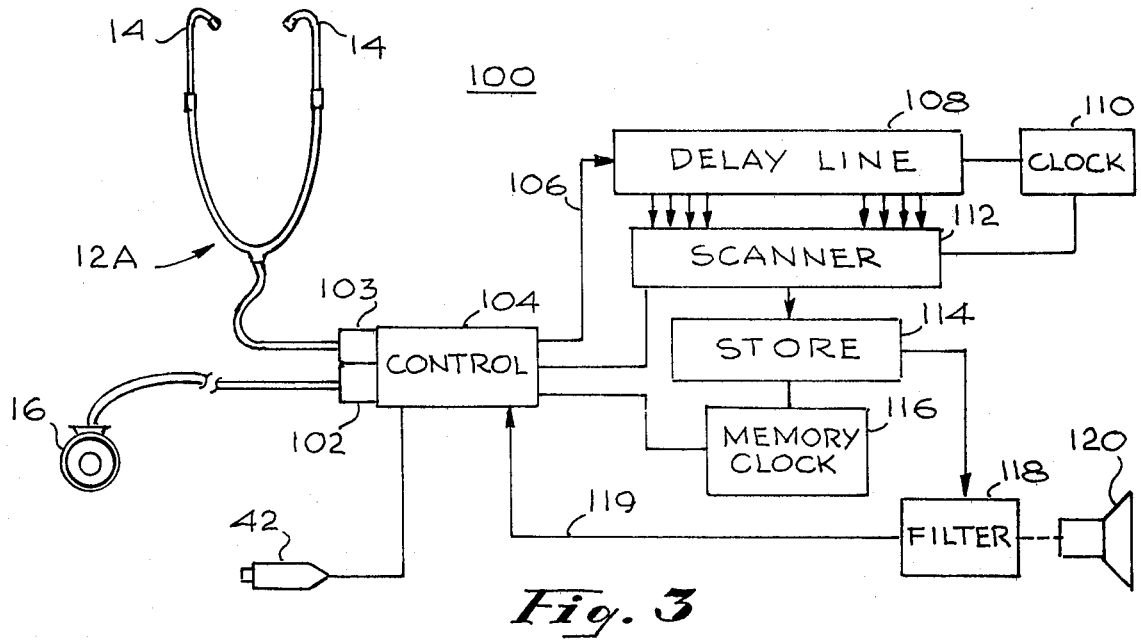
FIG. 3 is a block diagram of still another arrangement in accordance with the present invention utilizing a delay line and clocked memory device for sampling to store and read out at different rates.

FIG. 3 is a block diagram of a system 100 in accordance with the present invention utilizing a modified stethoscope 12A equipped with a standard pickup 16 and having an electro-acoustical transducer 102 as an input to a control stage 104. A signal path 106 extends from the control stage 104 to a delay line 108. This delay line 108 may be, for example, a Charge Coupled Device (CCD) delay line having the capability of shifting the input signals from the lead 106 through the delay line 108 in successive stages under the control of an associated clock 110. Such a delay line is well known in the art. As shown in FIG. 3, delay line 108 is equipped with a series of taps spaced at positions 0, 5, 10, 15, etc., the output of which is applied to a scanner 112 which is also controlled by the clock 110. The output of the scanner 112 is coupled to a store or memory device 114 controlled by a memory clock 116 which is also coupled to the control stage 104. The output of the memory 114 is applied to a filter 118 from which regenerated signals are fed to an output transducer 103 in the control stage 104 for conversion to sounds in the stethoscope 12A. As before, a push button switch 42 is connected to activate the control stage 104. As an alternative audio output, a speaker 120 is shown coupled to the filter 118.

In the operation of the system of FIG. 3, during the STORE mode, electrical signals from the transducer 102 are applied through the control stage 104 via the lead 106 to the delay line 108. These signals are also applied to the output transducer 103 and are heard as sounds in the earpieces 14 of the stethoscope 12A. If appropriate, the electrical signals may be suitably sampled before or at the time of entering the delay line 108. These pass through the delay line as a serial train of signals. The delay line taps are arranged to provide an output from discrete storage positions in the delay line 108 when triggered by the scanner 112. Caceres et al, in the article cited hereinabove, teach that an electrocardiogram wave form may be sampled at a rate of 625 samples per second without losing pertinent information. The same rate may be used for the sampling of a signal corresponding to audible heart sounds or, if desired, higher rates may be employed—perhaps in the range of 2000 to 4000 samples per second. Thus, the delay line taps in the system 100 are spaced to permit sampling of the heart sound signal stored in the delay line 108 at regular intervals spaced so as to derive all of the pertinent information in the heart sound wave form while realizing benefits of economy of storage in the memory device 114. A typical CCD delay line module may comprise 32 stages. A number of these modules may be connected in series to develop a delay line of sufficient length to store a suitable portion of the continuous heartbeat sound signal. When the delay line 108 has been filled to its signal capacity, the clock 110 triggers the scanner 112 and causes it to rapidly scan the taps from the delay line 108, beginning at the right-hand end (the beginning of the stored signal). The signals from the delay line taps are directed in serial fashion to the store 114 where they are stored in sequential memory cells. This process is repeated continuously so long as the stethoscope 12A is being used in conventional fashion. Whenever the capacity of the memory 114 is reached, the memory simply begins over again at the first cell and subsequent signal information is recorded over information previously stored.

Whenever the practitioner wishes to review a few heartbeat cycles, he presses the switch 42 which causes the control stage 104 to transfer the internal connection to the transducer 103 from the transducer 102 to the lead 119. At the same time, the control stage 104 causes the scanner 112 to block further signals from being directed to the store 114 and activates the memory clock 116 to begin reading out the information stored in the memory. However, the memory clock 116 operates at a lower clock rate as selected, for example 1/5 the rate of the clock 110, so that the signals being fed out of the memory 114 proceed at a rate 1/5 their real time rate. However, the pitch of the storage signals is unaffected. The filter 118 serves to smooth any transitions between signals from one memory cell to the next. The output of the filter 118 may be converted acoustically in the speaker 120 or may be applied via line 119 to the transducer 103 for conversion into acoustic signals. As long as the switch 42 is depressed, the signals stored in the memory 114 are repetitively read out and regenerated as acoustic signals, thus permitting the user to study a selected portion of stored heartbeat cycles, with natural sound but stretched-in-time.

As shown and described herein, arrangements in accordance with the present invention advantageously permit a physician or other practitioner, using a stethoscope-type instrument with which he is readily familiar, to listen to a patient's heart sounds in the usual manner and, when he wishes to review certain heart sounds stretched out in time, to "play back" the sound extended in time but without change in pitch. The review can be repeated as many times as desired to study a detected abnormality or other event of interest. Thus, his natural training directed to analysis of true heart sounds can be applied, without need for retraining or adaptation, to the reproduced sounds which are the same as the real time sounds but merely extended in time, thus facilitating the physician's analysis and diagnosis of any abnormal or unusual conditions evidenced by the sounds.

Although there have been described above specific arrangements of a stethoscope-type recording system with stretched-in-time playback in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention.

What is claimed is:

1. Apparatus for reproducing sounds stretched-in-time comprising:
   sound transducer means for picking up audible sounds and generating corresponding electrical signals;
   means for processing said electrical signals to develop a selected sequence of sample signals;
   means for recording the selected sample signals in a storage medium at a first rate;
   means for reproducing the same sample signals from the storage medium at a second rate which is slower than the first rate;
   means for regenerating an audible signal from the reproduced signals, which audible signal contains the frequency characteristics of the original audible sounds, including original pitch, but stretched-in-time; and
   selectively actuable control means coupled to control the recording means and the reproducing means to operate at different rates.

2. Apparatus of claim 1 further including control means coupled to the reproducing means for selectively activating the reproducing means.

3. Apparatus of claim 2 wherein the control means comprises a manually operable switch.

4. Apparatus of claim 2 wherein the control means includes an input sound transducer coupled to pick up audible sounds and an output transducer for regenerating audible signals from reproduced signals and, alternatively, from the input transducer.

5. Apparatus of claim 2 further including means for interrupting the application of the original audible sounds to the sound transducer means upon activation of the reproducing means.

6. Apparatus of claim 1 wherein the storage medium comprises a rotatable magnetic member and means for driving the member at a constant rotational speed relative to the recording and reproducing means.

7. Apparatus of claim 6 further including magnetic transducer means for converting between electrical signals and magnetic imprints on the storage medium.

8. Apparatus of claim 7 further including means for selectively driving the transducer means to develop translational motion of the transducer means relative to the rotatable member at one or another of two different speeds and control means coupled to control the selectively driving means.

9. Apparatus of claim 8 further including means for demodulating signals reproduced from the storage medium, the processing means and the demodulating means being selectively operable in response to the control means.

10. Apparatus of claim 9 further including means in series with the sound transducer means for selectively blocking the audible sounds, and means for activating the blocking means when signals are being reproduced from the storage medium.

11. Apparatus of claim 6 wherein the magnetic member comprises a magnetic drum, and wherein the magnetic transducer means comprises a transducer for recording imprints on the drum in successive side-by-side tracks, and further including means for driving a reproducing magnetic transducer across said tracks at a speed less than the recording transducer speed during recording.

12. Apparatus of claim 1 wherein the recording means comprises an endless loop tape recorder, wherein the processing means comprises an analog-to-digital converter for supplying discrete sample signals to the tape recorder, and wherein the audible signal regenerating means comprises a digital-to-analog converter coupled to the output of the tape recorder.

13. Apparatus of claim 12 wherein the control means is coupled to the tape recorder to selectively control the drive speed thereof.

14. Apparatus of claim 1 including means coupling the sound transducer means to an input of the control means and a head set coupled to receive electrical signals alternatively from the sound transducer means and from the signal reproducing means via the control means.

15. Apparatus of claim 1 wherein the processing means comprises a delay line for temporarily storing discrete sample signals in sequence, wherein the recording means includes a scanner for transferring signals from the delay line to the storage medium, and wherein the reproducing means includes a memory clock for driving the storage medium to reproduce signals for application to the audible signal regenerating means.

16. Apparatus of claim 15 further including a delay line clock for shifting signals through the delay line and the scanner in synchronized sequence.

17. Apparatus of claim 16 wherein the delay line clock and the memory clock are operable at different pulse rates, the memory clock being selectively operable from the control means.

18. A heart sound processing system comprising:
   a pickup for heart sounds;
   a transducer associated with said pickup for developing electrical signals corresponding to the heart sounds;
   means for recording and reproducing said electrical signals;
   means for selectively controlling the recording and reproducing means to record the signals in real time and to reproduce a selected portion of the recorded signals at a later time with original pitch but stretched-in-time;
   means for generating audible sounds from applied electrical signals; and
   means for selecting between the original heart sounds and the reproduced signal portion for application to a user's ear.

* * * * *